United States Patent [19]

Hein et al.

[11] Patent Number: 5,771,909
[45] Date of Patent: Jun. 30, 1998

[54] PROGRAM CONTROLLED DISHWASHER

[75] Inventors: Wolfgang Hein; Ulrich Hettenhausen, both of Bielefeld; Frank Kethers, Lage/Lippe; Peter Obermeier, Bielefeld, all of Germany

[73] Assignee: Carl Miele & Cie. GmbH & Co., Guetersloh, Germany

[21] Appl. No.: 635,500

[22] Filed: Apr. 22, 1996

[30]     Foreign Application Priority Data

Apr. 22, 1995 [DE]  Germany .................. 195 14 873.8

[51] Int. Cl.$^6$ ...................................................... B08B 3/02
[52] U.S. Cl. .................... 134/57 D; 134/58 D; 134/131; 134/165; 134/201
[58] Field of Search ................................ 134/57 D, 58 D, 134/56 D, 44, 131, 56 R, 57 R, 58 R, 61, 140, 165, 201

[56]          References Cited

U.S. PATENT DOCUMENTS

| | | |
|---|---|---|
| 3,530,864 | 9/1970 | Wright .................................. 134/58 D |
| 4,114,190 | 9/1978 | Mazuir .................................. 134/57 D |
| 4,561,904 | 12/1985 | Eberhardt, Jr. ........................ 134/57 D |
| 5,000,207 | 3/1991 | Titterington et al. ..................... 134/44 |
| 5,267,580 | 12/1993 | Payzant ................................. 134/58 D |
| 5,287,866 | 2/1994 | Torimitsu et al. ..................... 134/57 D |

*Primary Examiner*—Frankie L. Stinson
*Attorney, Agent, or Firm*—Karl Hormann

[57]           ABSTRACT

A program controlled dishwasher in which magnetic sensors provided adjacent to the dishwasher door respond to magnetic fields of predetermined polarization provided by permanent magnets in a catenulate magnetic key mounted on a dishwasher caddy in a position adjacent the magnetic sensors when the caddy is in the tub of the dishwasher, for generating a verifiable code pattern readable against dishwasher stored programs for the selection and actuation of a program specific to the articles which are stored in the caddy for washing. The polarization patterns on the caddies are specific to the kind of articles stored therein and may be readily altered to accommodate different articles.

26 Claims, 3 Drawing Sheets

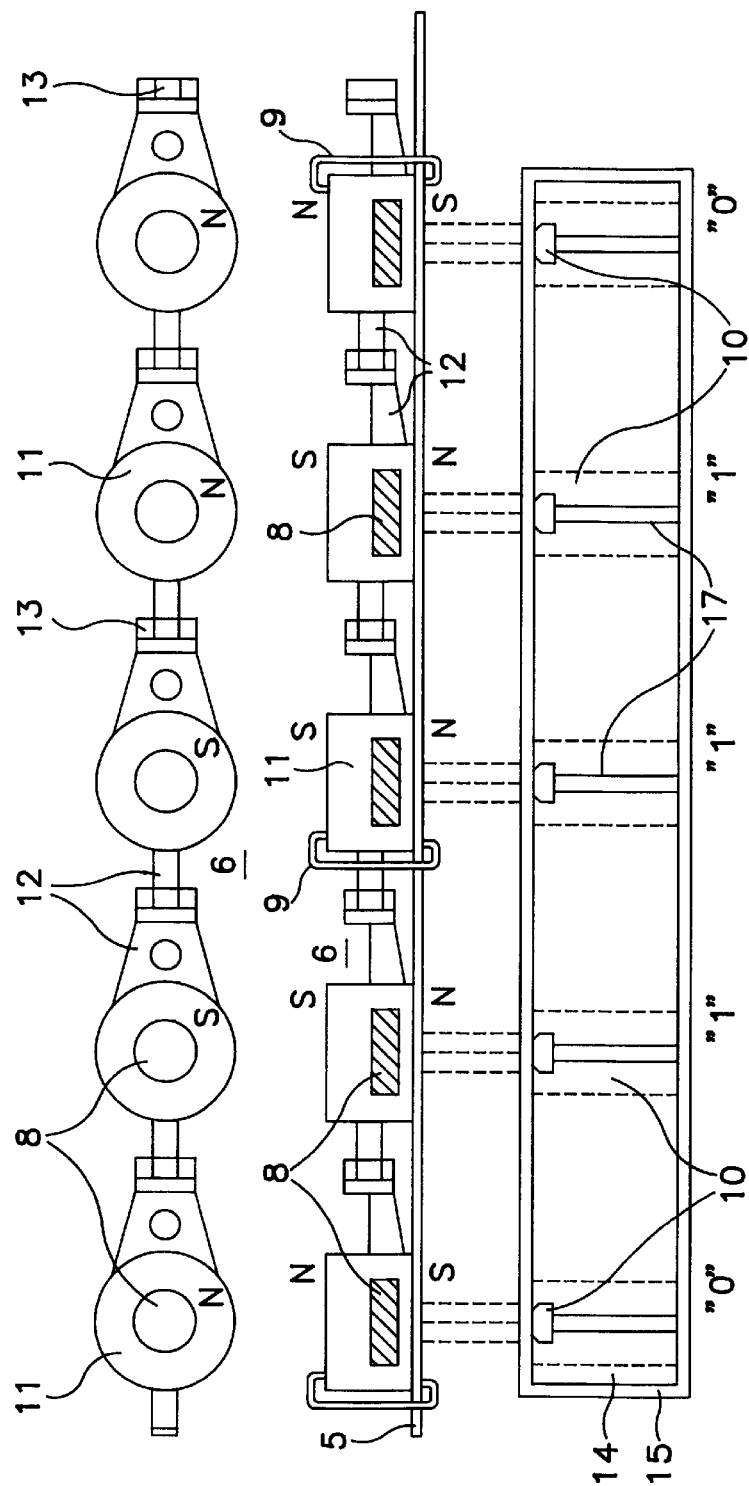

| Codemuster (5-Bit) 1. 2. 3. 4. 5. | | | | | Progr. PG |
|---|---|---|---|---|---|
| 1 | 1 | 1 | 0 | 0 | 1 |
| 1 | 1 | 0 | 1 | 0 | 2 |
| 1 | 0 | 1 | 1 | 0 | 3 |
| 0 | 1 | 1 | 1 | 0 | 4 |
| 1 | 1 | 0 | 0 | 1 | 5 |
| 1 | 0 | 1 | 0 | 1 | 6 |
| 0 | 1 | 1 | 0 | 1 | 7 |
| 1 | 0 | 0 | 1 | 1 | 8 |
| 0 | 1 | 0 | 1 | 1 | 9 |
| 0 | 0 | 1 | 1 | 1 | 10 |

FIG. 6

| Codemuster (4-Bit) 1. 2. 3. 4. | | | | Paritäts Bit | Progr. PG |
|---|---|---|---|---|---|
| 1 | 0 | 0 | 0 | 1 | 1 |
| 0 | 1 | 0 | 0 | 1 | 2 |
| 1 | 1 | 0 | 0 | 0 | 3 |
| 0 | 0 | 1 | 0 | 1 | 4 |
| 1 | 0 | 1 | 0 | 0 | 5 |
| 0 | 1 | 1 | 0 | 0 | 6 |
| 1 | 1 | 1 | 0 | 1 | 7 |
| 0 | 0 | 0 | 1 | 1 | 8 |
| 1 | 0 | 0 | 1 | 0 | 9 |
| 0 | 1 | 0 | 1 | 0 | 10 |
| 1 | 1 | 0 | 1 | 1 | 11 |
| 0 | 0 | 1 | 1 | 0 | 12 |
| 1 | 0 | 1 | 1 | 1 | 13 |
| 0 | 1 | 1 | 1 | 1 | 14 |
| 1 | 1 | 1 | 1 | 0 | 15 |

FIG. 7

PROGRAM CONTROLLED DISHWASHER

BACKGROUND OF THE INVENTION

1. Field of the Invention

The invention, in general, relates to a program controlled dishwasher and, more particularly, to a dishwasher of the kind provided with indicia for programming the operation of the dishwasher in correspondence with the kind of dishes to be washed.

The dishwasher in accordance with the invention is particularly useful for the program-controlled cleaning, sterilization or disinfection and drying of articles to be washed, such as, for example, respiratory hoses, catheters, surgical instruments, pipettes and the like, which for treatment within the enclosed chamber of the automatic dishwasher have to be sorted into special caddies or separate baskets, each caddy or basket being provided with a magnetic key the magnetization of which is determinative of the program controlling the washing or other treatment of the articles in the caddy or basket.

2. The Prior Art

German published patent specification DE-OS 27 01 879 discloses a dishwasher provided with a key at the rear of the dish storing basket for setting of the washing program. The key consists of a magnetic pin the magnetization of which is determinative of a given washing program. The storage baskets used in this machine are designed to take up a particular kind of dishes. The special basket design for particular dishes in combination with the magnetic key ensures the setting of an appropriate washing program. For this purpose, there is associated with the magnetic pin a complementary lock provided at the rear wall of the tub or washing chamber for reading the magnetic pattern of the magnetic pin of a basket or caddy inserted in the tub. The disadvantage of such an arrangement is that changing the dishwasher program requires a complete exchange of the magnetic pin for a differently encoded pin. This, in turn, requires many different individual magnetic pins.

From German patent DE-PS 35 16 006 it is known for the individual setting of programs in washing and disinfection apparatus to arrange, on a caddy, individual magnets in a predetermined combination, permanent magnets being added or removed depending upon any given combination. These individually mountable or removable permanent magnets are arranged either at a side or at the front of the frame of a caddy, in facing relationship with the rear wall of the tub. The magnets activate or switch a plurality of reed switches arranged at the rear or lateral wall of the tub of the apparatus. The disadvantage of such an arrangement is that the position of the permanent magnets at the rear or at the side of the caddy requires a complementary placement of the magnetic switches (reed contacts) at the rear or lateral exterior side of the apparatus. Since in a laboratory or surgical setting, the rear and lateral sides of dishwashers are usually confined by an abutting wall of the room and closely abutting apparatus and cabinets, respectively, such a spatial arrangement of program selection elements can hardly be considered to be an easily serviceable one. For an exchange or controlled adjustment of the switching elements, the heavy dishwasher would, with considerable effort, have to be pulled out of its installation space, which is rather an involved operation and which, for reasons of time and costs, is neither desirable nor tolerable. In addition, the arrangement of individual magnets on the basket or caddy requires corresponding individual brackets, which impede an efficient manufacture of differently configured baskets and caddies. Also, individually mountable permanent magnets may fall of a caddy and become lost. Moreover, reed contacts have no precisely defined switching points are sensitive to stray fields which may possibly lead to faultily controlled programs. In machine washing and cleaning as well as in the disinfection of articles used in surgery or in laboratories it is particularly important to ensure that no false washing programs are released. Incorrectly initiated programs are similar to faulty handling which may lead to the destruction of delicate and costly articles. In the known control it is also not possible to determine whether the signals released by the magnets or reed contacts are correct.

OBJECTS OF THE INVENTION

It is, therefore, a primary object of the invention to provide a program controlled automatic dishwasher which avoids the disadvantages of prior art apparatus.

A more particular object of the invention resides in the provision of a dishwasher program control which requires no individually mountable or removable permanent magnets.

Yet another object is to provide a program controlled dishwasher of the kind under consideration which allows a quick and, simple selection of a program for any given basket or caddy inserted into the dishwasher.

Still another object is to provide a program controlled dishwasher which effectively prevents the initiation of incorrect program cycles.

Another object is to provide a program controlled dishwasher which prevents an incorrect program initiation even where structural components of the control selection circuit are defective.

It is also an object of the invention to provide a program controlled dishwasher which prevents an incorrect program initiation even where components of the program selection circuit switch incorrectly.

BRIEF SUMMARY OF THE INVENTION

In the accomplishment of these and other objects the invention provides for a program controlled dishwasher of the kind referred to, in which a magnetic key provided on a caddy or basket comprises a magnetic bar including a plurality of permanent magnets the individual magnetic alignments (north-south/south-north) of which can be altered.

In a particularly advantageous embodiment of the invention a magnetic key member may be removably mounted on a portion of a dishwasher caddy or basket facing the door thereof. Magnetic sensors for reading the magnetic polarity of the key member may be provided adjacent to the door of the dishwasher.

Other objects will in part be obvious and will in part appear hereinafter.

As will hereafter appear, particular advantages to be derived from practicing the invention are, inter alia, that dishwasher caddies and baskets may easily and quickly be adjusted to predetermined washing programs and the like. Any magnetic key member may be used repeatedly on a given caddy or basket. Furthermore, the use of magnetic sensors which are capable of selectively recognizing the magnetic polarity or flux pattern of the magnetic key member ensures that no incorrect program will be selected by a basket or caddy, hence providing for improved safety for the articles to be washed or otherwise treated.

BRIEF DESCRIPTION OF THE SEVERAL DRAWINGS

The novel features which are considered to be characteristic of the invention are set forth with particularity in the appended claims. The invention itself, however, in respect of its structure, construction, and lay-out, as well as manufacturing techniques, together with other objects and advantages thereof will be best understood from the ensuing description of the preferred embodiments, when read in conjunction with the appended drawing, in which:

FIG. 2 is a top elevation view of a magnetic key member comprising a magnetic bar for use with a caddy;

FIG. 3 depicts the key member as mounted on a caddy;

FIG. 4 shows magnetic sensors on the dishwasher for activation by the magnetic key member on a caddy;

FIG. 6 is a table of readable code patterns for the selection of programs generated by the magnetic sensors;

FIG. 7 another table of readable code patterns for a selection of programs; and

Figure 8:
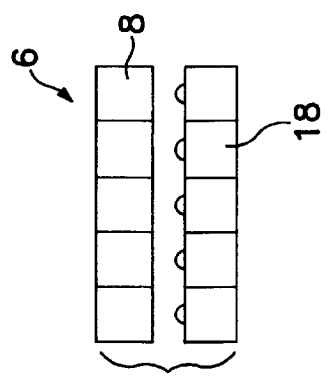

FIG. 8 is a schematic view, in side elevation, of a magnetically responsive microswitch.

DETAILED DESCRIPTION OF THE SEVERAL EMBODIMENTS

Figure 1:
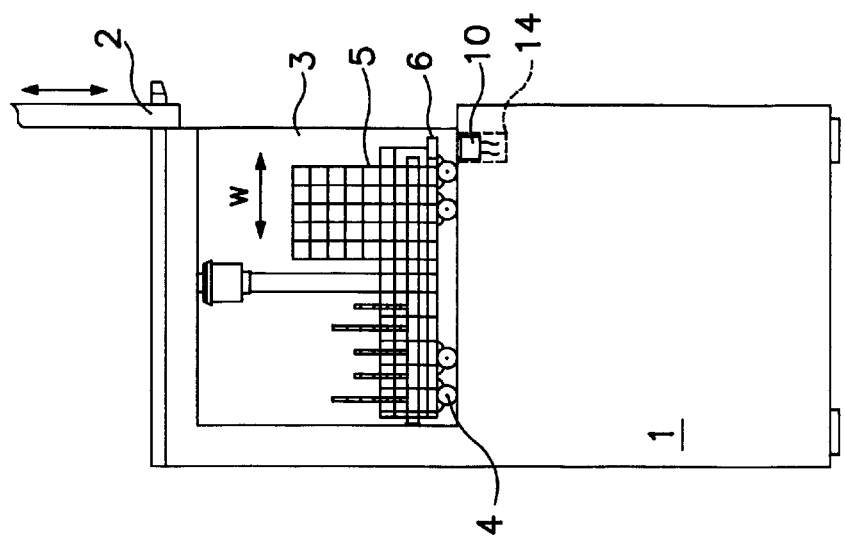
FIG. 1 is a side view, with parts broken away, of a dish washer with a caddy for receiving articles to be washed positioned in the open washing chamber.

While FIG. 1 depicts an automatic dishwasher 1 of the kind particularly useful in laboratories or hospitals, the invention is not limited to such apparatus. Rather, and as used herein, the term dishwasher is intended to include ordinary household dishwashers as well as specialized apparatus capable of sterilizing, disinfecting and drying articles treated thereby, in addition to cleaning them. Thus, such terms as washing program, washing cycle and the like hereinafter used from time to time, are intended also to include or connote other operations in connection with the treatment or recycling of dishes, laboratory equipment and so on. The dishwasher 1 is provided with a washing chamber or tub 3 which in the embodiment shown may be closed by a sliding door 2. The tub serves to clean, sterilize, and dry in a well-known manner articles to be washed such as respiratory hoses, catheters, surgical instruments, pipettes and the like. These articles (not shown) are sorted into a basket or caddy (5) provided wheels 4, for treatment in the tub 3 of the apparatus 1. For the treatment of the articles within the automatic dishwasher 1 a plurality of separately invocable cleaning and sterilization programs are provided, e.g. stored in a read-only memory, which may be called up by the articles or basket or caddy in which they are stored. Accordingly, different types of baskets or caddies are required. To this end, each basket or caddy 5, hereinafter collectively referred to as caddy, designed for receiving a particular kind of article, is provided with a magnetic key member 6 (FIG. 2) the magnetization of which determines the washing program for the articles stored within the caddy. By removing the key member 6, its pattern of magnetization ay be altered.

Figure 5:
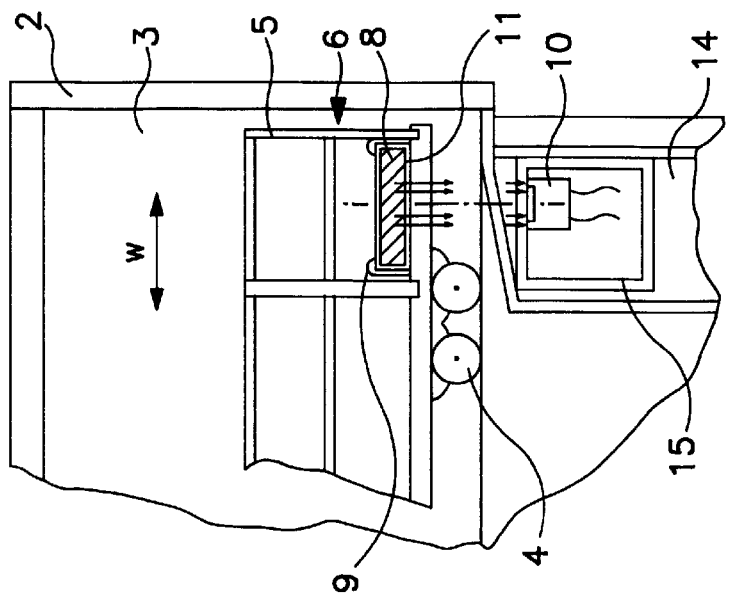
FIG. 5 is a schematic view, partially in section, of a permanent magnet on a caddy in an operational position relative to a magnetic sensor on a dishwasher.

As may be seen by reference to FIGS. 1, 3 and 5, the magnetic key member 6 is mounted on that portion of the caddy frame 7 which is positioned adjacent to the door 2 of the dishwasher 1. The key member 6 is constituted by an integral flat strip or bar mounting a plurality of separate permanent magnets 8. The pattern or direction of magnetization of each permanent magnet 8 of the key member 6 is selectable and changeable; but for a given caddy 5 serving or setting a particular program, the direction of magnetization, e.g., north-south/south-north, it is predetermined. Preferably, the number of permanent magnets in the bar on each caddy 5 is the same, but their polarization pattern, i.e., the direction of the magnetic flux, of individual magnets differs in accordance with a selected washing program. Thus, their polarization differs, as shown, for instance, in FIGS. 2 and 3. To facilitate altering the disposition of the polarity of individual magnets, the magnetic key 6 is removably mounted at a forward portion of the caddy 5 positioned adjacent to the door 2 of the apparatus 1. The magnetic key 6 may be releasably mounted on the caddy 5 by retaining clamps 9 or the like. In this manner, otherwise necessary alterations on mass-produced caddies 5 not yet provided with a key 6 are avoided.

The permanent magnets 8 of a magnetic bar are held together in a catenulate manner to form a key 6, and within the chain they are arranged for individual rotation about their axes thereby to change their polarity relative to magnetically responsive sensors 10. The caddies 5 may thus simply and quickly be coded to predetermined cleaning or washing programs. The magnetic keys 6 of each caddy may be used repeatedly. Preferably, the individual links of the magnetic keys 6 are inseparably connected to each other so that each key may be considered to be an integral unit, individual permanent magnets 8 of which can neither be lost nor separate from a caddy 5. On the other hand, in certain circumstances key members 6 consisting of separable chain links may be desirable. Such separable links would preferably be provided, however, with safety locks or catches between individual links.

Every one of the permanent magnets 8 of a magnetic bar is received in a bracket 11 formed, for instance, of polymeric non-magnetizable material and is provided on opposite sides thereof with laterally extending integral connecting members 12. The connecting members 12 are connected to each other for a 180° or 360° rotation. The members 12 may be connected to each other in a particularly simple manner by snap connections 13. The permanent magnets 8 received in the brackets 11 are seen in FIGS. 3–5 to be of a disk-shaped configuration so that they may be flush-mounted on the non-magnetic frame of a caddy, thereby ensuring a constant distance relative to adjacent magnetic sensors 10. The frames of such caddies are usually made of stainless steel.

The arrangement of the magnetic bars or magnetic key members 6 on the frame of a caddy is preferably chosen such that the disposition of the magnetic field, or the flux line, of each magnetic pole cooperating with the magnetic sensors 10 extends transversely of, or normal to, the direction of movement (arrow W, FIG. 1 or 5) of a caddy 5. To this end, the magnetic sensors 10 to be actuated by the magnets are preferably disposed exteriorly of the tub 3, within the door 2 or in a chamber 14 provided below the opening of the tub 3 (FIG. 4 and 5), adjacent the door 2. The chamber 14 is preferably accessible from behind the front panel or cladding of the dishwasher 1. The magnetic sensors 10 generate readable code patterns for a washer program, corresponding to the magnetic polarities of the magnetic key member 6. In case it is desired, for instance, to enlarge the selection of programs, the number of magnetic sensors is preferably chosen to be greater than the number of permanent magnets of any magnetic key member. However, in the embodiment shown, the number of magnetic sensors 10 is equal to the number of permanent magnets 8 of a magnetic key member 6.

For the sake of easy maintenance the magnetic sensors 10 are preferably mounted in a forwardly disposed hollow rail member 15 (FIG. 2) within the chamber 14 below the bottom 16 of the tub 3. Thus, by removing the front panel of the dishwasher, adjustments in the position of the scanning system can be performed in a controlled manner, since an adjustment in the position of the magnetic sensors 10 can always be performed relative to a given position or alignment of the magnetic bar on a caddy 5, and vice versa.

By utilizing a door 2 pivoting downwardly (not shown) at the front of the dishwasher 1, the magnetic sensors 10 may be positioned inside the door 2, between its interior and exterior sheet-metal linings or panels. Such an arrangement also facilitates servicing or maintenance. When the door 2 of the dishwasher 1 is closed, the magnetic sensors 10 will have been moved into the active range of the permanent magnets 8 of the magnetic key member 6, so that the code pattern of the caddy 5 may be read and verified by the system at the initiation of a program.

Preferably, the magnetic sensors 10 actuated by the magnetic key members 6 are Hall sensors which can identify the individual polarities (north-south/ south north) of the permanent magnets 8 directly and generate verifiable code patterns based on the magnetic polarities, for the selection of a washing program. In contrast to known reed contacts, such Hall sensors have not only a precisely defined switching point, but they also operate in a more reliable manner in elevated temperature ranges, and they may be designed to recognize the north pole "N" of a permanent magnet 8 of the magnetic key member 6 either as log "1" (logic "one") or as log "0" (logic "nil"). For the embodiment of the magnetic sensors 10 herein described, a signal is generated at logic "1". In that state the north pole "N" of the permanent magnet 8 is aligned with the magnetic sensor 10, and the south pole "S" of the permanent magnet 8 points upwardly in the caddy 5 (FIG. 3, 4 and 5). In contrast to reed switches which as magnetic switches which will always switch in the presence of a magnetic field or even of an undesirable stray field, regardless of the direction of their flux or the north or south pole generating those fields, Hall sensors may be set as magnetic sensors to respond to a given polarity by reacting either as logic "1" or logic "0". Thus, easily and simply recognizable code patterns can be generated by such Hall sensors in combination with the magnetic key members affecting them.

Micro switches the toggles of which are either provided with individual magnets or which may be directly influenced by magnetic forces, may also be used as magnetic sensors with substantially the same effect. Where such microswitches 18 are provided with individual magnets, they would every one of them be polarized such that their north poles "N" point in the direction of the magnetic key member 6 mounted on the caddy 5. In such an arrangement it is important that the reset or retractive force of the toggle exceeds the force of the magnet. The microswitch will remain open, at logic "0" or "nil", when the magnetic sensor 10 is not activated. A switching operation is accomplished by the repelling magnetic forces of the interactive magnetic fields of the permanent magnets 8 at the caddy 5 and of the magnet of the micro switch. Such a magnetic sensor 10 will also recognize, or respond to, the disposition of the polarity of the permanent magnet 8 facing it. Where a north pole "N" of the magnet of the magnetic bar meets a north pole "N" of the micro switch, the microswitch is actuated and releases a log "1" signal, which in combination with the signals from the other micro switches generates the readable code pattern for the washing program. On the other hand, the reset force of the toggle may be less than the force of the magnet. In such a case the microswitch is closed when the magnetic sensor is not activated (log "1"). A switching operation is then accomplished by the attractive magnetic forces of the magnetic fields. An example of a microswitch and its arrangement relative to a permanent magnet of a key member 6 is schematically shown in FIG. 8.

By way of the magnetic sensors 10, such as, for instance, the Hall sensors or microswitches provided with toggles actuable by magnetic forces, activated by the magnetic key members 6, code patterns (FIGS. 4 and 6, 7) may be generated which correspond in number to the stored or selectable washing or other programs. The generated code patterns can be read and verified against comparison code patterns retrievably stored in a program memory, such as a read-only memory (ROM) (not shown) of the dishwasher 1. Such verification and comparison is always performed prior to the start of a program. To ensure that it is always a correct program which is called up by a magnetic key 6, the digital code patterns generated by the magnetic keys 6 are compared against the stored patterns before a program is started, and only when concurrence is established will a program be initiated.

The validity examination of the code patterns is based upon certain rules. For instance, the rules may be such that a code pattern is only accepted as valid if an equal number of log "1" or log "0" is always generated. Where the rule is not satisfied, an error signal is released, it being assumed that the magnetic bars are all equipped with the same number of magnets, for instance, five permanent magnets 8 corresponding to five magnetic sensors 10.

Corresponding valid code patterns which can be generated as a five-bit code word are depicted in the table of FIG. 6. In accordance with this table, caddies 5 or their magnetic keys 6 may select from between ten different programs for treating articles. Advantageously, the system is rendered failsafe by the fact that only those code patterns are valid which have the same number of log "1". In the instant example, these are those code patterns in which log "1" occurs three times. If a log "1" signal in a codeword transitions to a log "0", it can only be because of an error condition. The sum of the generated log "1" does not equal 3. Such a code pattern is detected and rejected by the system. On the other hand, a transition from a log "0" to a log "1" also releases an error signal and prevents the start of a program.

As shown in FIG. 7, the verifiable code patterns can also be based upon a condition in which code patterns generated as a four-bit code word are supplemented by a parity bit. The parity bit becomes log "1" if the sum of log "1" signals is uneven, and it becomes log "0" if the sum of log "1" signals is even. FIG. 7 depicts the possibility of selecting a total of fifteen programs or code patterns, a four-bit code word being supplemented by a parity bit (log "1" or log "0") .

FIG. 3 depicts an alignment of the individual polarities "S"-"N"-"N"-"N"-"S" of the permanent magnets 8 of a magnetic key member 6 for generating a five-bit code pattern in accordance with the bit combination log "0"-log "1"-log "1"-log "1"-log "0", or for selecting the 4th program (article treatment program 4) from Table 6). The code pattern is generated by five magnetic sensors 10 (FIG. 4).

On the other hand and provided the magnetic sensors respond to the polarities shown in top elevation, the alignment "N"-"S"-"S"-"N"-"N" in FIG. 2 of individual polarities, will generate a verifiable code pattern comprising the bit combination log "1"-log "0"-log "0"-log "1"-log "1", which would lead to the selection of the 8th program in Table 6 (PG 8).

In order to ensure optimum exposure of the magnetic sensors 10 to the magnetic fields of the magnetic bars on the caddies 5 and thus respond to them, each sensor is additionally provided with a focussing mirror or reflector 17 for focussing of the magnetic fields, as seen in FIG. 4. In this manner, any possible extraneous influence on the magnetic fields, as, for instance, from magnetically conductive articles, may be effectively overcome.

It will be apparent to those skilled in the art that the magnetic key member in accordance with the invention cooperating with magnetic sensors for recognizing the polarity of individual magnets may equally advantageously be utilized in household dishwashers. Particular applications may result from special caddies or inserts, such as a lower caddy for pots and pans and an upper caddy for delicate glassware requiring an especially delicate washing cycle, calling up individual caddy or insert related programs.

It will also be apparent that other changes and alterations may be performed without departing from the spirit of the disclosed invention.

What is claimed is:

1. An apparatus for cleaning, sterilizing and drying of articles under the control of a predetermined program selected from a plurality thereof, comprising:

cavity means defining a wash chamber;

means movable relative to said wash chamber for storing said articles;

magnetic key means provided with a predetermined pattern of magnetization determinative of said predetermined program for washing, sterilizing and drying said articles in said storing means, said magnetic key means comprising a plurality of individual magnetic means of predetermined magnetic polarities; and means for releasably mounting said magnetic key means on said storing means.

2. The apparatus of claim 1, wherein said magnetic means comprises permanent magnets.

3. The apparatus of claim 1, wherein said magnetic polarities may be individually altered.

4. The apparatus of claim 3, wherein said plurality of individual magnetic means are linked to each other in a chain-like manner.

5. The apparatus of claim 4, wherein said plurality of individual magnetic means are individually mounted in non-magnetic support means linked to each other.

6. The apparatus of claim 5, wherein said magnetic means are of disk-like configuration.

7. The apparatus of claim 6, wherein said polarity of said individual magnetic means relative to each other is altered by the selective rotation thereof.

8. The apparatus of claim 7, wherein said support means are inseparably linked to each other.

9. The apparatus of claim 7, wherein said support means are rotatably connected to each other by lateral extensions.

10. The apparatus of claim 9, wherein said extensions are snap-fitted to each other.

11. The apparatus of claim 1, wherein said cavity means is provided with door means and wherein said magnetic key means is mounted on said storing means for placement adjacent to said door means when said storing means is in said washing chamber.

12. The apparatus of claim 11, further comprising means provided adjacent to said door means for responding to said magnetic key means.

13. The apparatus of claim 12, wherein said responding means comprises magnetic sensor means adapted to respond to said polarities of said individual magnetic means for generating a code pattern based on said polarities.

14. The apparatus of claim 13, wherein said magnetic sensor means is of a number corresponding to said plurality of said individual magnetic means.

15. The apparatus of claim 14, further comprising means for accessibly storing said plurality of washing, sterilizing and drying programs.

16. The apparatus of claim 15, wherein said code patterns are verifiable against said stored programs for selecting said predetermined program.

17. The apparatus of claim 11, further comprising a chamber below said cavity for retaining said magnetic sensor means.

18. The apparatus of claim 1, wherein said magnetic sensor means is mounted inside said door means.

19. The apparatus of claim 1, wherein said storing means comprises a plurality of caddy means individually movable relative to said washing chamber.

20. The apparatus of claim 19, wherein each one of said plurality of storing means is provided with magnetic key means having individual magnetic means of different relative polarities.

21. The apparatus of claim 1, wherein said polarities of said individual magnetic means provide for magnetic fields extending substantially normal to the direction of relative movement of said storing means.

22. The apparatus of claim 1, wherein said magnetic sensor means comprises Hall sensors.

23. The apparatus of claim 1, wherein said magnetic sensor means comprises microswitch means provided with magnetically actuable switch toggles.

24. The apparatus of claim 1, wherein means is provided for focussing the magnetic force of said individual magnetic means on said magnetic sensor means.

25. The apparatus of claim 1, wherein said plurality of individual magnetic means provides predetermined code patterns of log "1" and log "0" signals totaling an equal plurality.

26. The apparatus of claim 25, wherein said code patterns are supplemented by a parity bit.

* * * * *